United States Patent [19]

Inoue et al.

[11] Patent Number: 4,752,413
[45] Date of Patent: Jun. 21, 1988

[54] 2-(ALKYLOXYCARBONYLOXYPHENYL)-5-ALKYLPYRIDINE AND COMPOSITION CONTAINING SAME

[75] Inventors: Hiromichi Inoue; Takashi Inukai; Kouji Ohno; Shinichi Saito; Kazutoshi Miyazawa, all of Yokohamashi, Japan

[73] Assignee: Chisso Corporation, Tokyo, Japan

[21] Appl. No.: 54,394

[22] Filed: May 26, 1987

[30] Foreign Application Priority Data

May 24, 1986 [JP] Japan .................. 61-120009

[51] Int. Cl.⁴ .................. C09K 19/34; C02F 1/13; C07D 211/70; C07D 211/82
[52] U.S. Cl. .................. 252/299.61; 252/299.5; 252/299.01; 350/350 R; 350/350 S; 546/339; 546/340; 546/342
[58] Field of Search .......... 252/299.61, 299.5, 299.01; 350/350 R, 350 S; 546/339, 340, 342

[56] References Cited

U.S. PATENT DOCUMENTS

| 4,659,500 | 4/1987 | Sugimori et al. | 252/299.61 |
| 4,668,426 | 5/1987 | Demus et al. | 252/299.61 |
| 4,684,220 | 8/1987 | Shionozaki et al. | 252/299.61 |
| 4,684,477 | 8/1987 | Sugimori et al. | 252/299.61 |

FOREIGN PATENT DOCUMENTS

| 56501 | 7/1982 | European Pat. Off. | 252/299.61 |
| 206228 | 12/1986 | European Pat. Off. | 252/299.61 |
| 228303 | 7/1987 | European Pat. Off. | 252/299.61 |
| 233706 | 8/1987 | European Pat. Off. | 252/299.61 |
| 239403 | 9/1987 | European Pat. Off. | 252/299.61 |
| 3515373 | 11/1986 | Fed. Rep. of Germany | 252/299.61 |
| 8606401 | 11/1986 | PCT Int'l Appl. | 252/299.61 |
| 2092169 | 8/1982 | United Kingdom | 252/299.61 |
| 1063101 | 6/1985 | U.S.S.R. | 252/299.61 |
| 1063100 | 6/1985 | U.S.S.R. | 252/299.61 |

OTHER PUBLICATIONS

Pavluchemko, A. I., et al, Advances in Liquid Crystal Research and Applications, Bata, L. Ed., Pergamon Press, Oxford, (1980).
Pavluchemko, A. I., et al, J. De Phys., Coll. C3, Suppl. 4; vol. 40, pp. C3-1-4, (Apr. 1979).

*Primary Examiner*—Teddy S. Gron
*Attorney, Agent, or Firm*—Wenderoth, Lind & Ponack

[57] ABSTRACT

A novel liquid crystal compound exhibiting smectic phases and useful for display elements and a chiral smectic liquid crystal composition containing the compound are provided, which compound is expressed by the formula

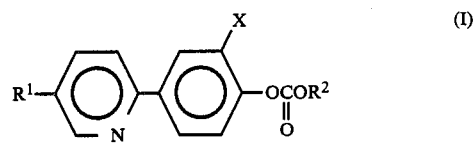

wherein $R^1$ and $R^2$ each represent an alkyl group of 1 to 20 carbon atoms and X represents H atom or F atom, and which composition comprises at least one kind of the compounds of the formula (I) and an optically active compound.

7 Claims, No Drawings

2-(ALKYLOXYCARBONYLOXYPHENYL)-5-ALKYLPYRIDINE AND COMPOSITION CONTAINING SAME

BACKGROUND OF THE INVENTION

1. Field of the Invention

This invention relates to a novel liquid crystal compound useful for display elements and a chiral smectic liquid crystal composition comprising the above liquid crystal compound and an optically active compound.

2. Description of the Prior Art

At present, as to liquid crystal display elements, TN (Twisted Nematic) type display mode has been most broadly employed, but as far as the response speed is concerned, such TN type display elements are inferior to emissive type display elements (such as those of electroluminescence, plasma display, etc.). Although various improvements in this respect have been attempted, it appears that possibility of the improvement to a large extent has not been left behind so much. Thus, various liquid crystal display devices based on a different principle from that of TN type display elements have been attempted. As one of such devices, there is a display mode utilizing a ferroelectric liquid crystal (N.A. Clark et al: Applied Phys. lett., 36, 899 (1980)). This mode utilizes the chiral smectic C phase (SC* phase), chiral smectic F phase (SF* phase), chiral smectic I phase (SI* phase), chiral smectic G phase (SG* phase) or chiral smectic H phase (SH* phase) of the ferroelectric liquid crystal, and those having these phases in the vicinity of room temperature are preferred.

These chiral smectic liquid crystal materials may be obtained by blending a plurality of single substances exhibiting chiral smectic phases by themselves, but it has been known that the above liquid crystal materials may also be constituted by adding an optically active compound, preferably an optically active liquid crystal compound, more preferably a chiral smectic liquid crystal compound to an achiral smectic liquid crystal (such as those having SC phase, SF phase, SI phase, SG phase, SH phase or the like).

As to liquid crystal compounds exhibiting smectic phases, various kinds thereof have already been known, but as to whether or not the chiral smectic liquid crystal materials obtained by adding thereto an optically active compound exhibit fully superior performances in ferroelectric liquid crystal displays, no ultimate evaluation has yet been obtained. This is due to the fact that liquid crystal displays utilizing ferroelectric properties have not yet been technically completed. Thus, in the present status, it is necessary to examine various kinds of new smectic liquid crystal compounds.

SUMMARY OF THE INVENTION

The main object of the present invention is to provide a novel liquid crystal compound exhibiting smectic phases and suitable to the above-mentioned use applications.

The present invention resides in
a liquid crystal compound expressed by the formula

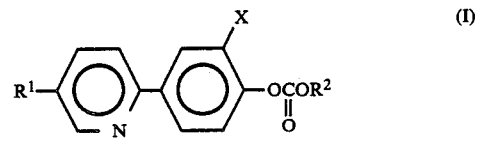

wherein $R^1$ and $R^2$ each represent an alkyl group of 1 to 20 carbon atoms and X represents hydrogen atom or fluorine atom, and a chiral smectic liquid crystal composition comprising at least one kind of the liquid crystal compound (I) and an optically active compound.

DETAILED DESCRIPTION OF PREFERRED EMBODIMENTS

Phase transition points of representatives of the compounds of the formula (I) are shown in Table 1.

TABLE 1

| Sample No. | In formula (I) $R^1$ | $R^2$ | X | Phase transition point (°C.) C | SE | SG | SB | SC | SA | N | I |
|---|---|---|---|---|---|---|---|---|---|---|---|
| 1 | $C_7H_{15}$ | $C_5H_{11}$ | H | ·48.4 | — | — | (·20.9) | — | (·25.8) | ·47.3 | · |
| 2 | $C_7H_{15}$ | $C_7H_{15}$ | " | ·47.1 | — | — | — | — | — | ·51.4 | · |
| 3 | $C_7H_{15}$ | $C_9H_{19}$ | " | ·36.3 | — | ·37.8 | — | — | ·39.0 | ·54.7 | · |
| 4 | $C_8H_{17}$ | $C_3H_7$ | " | ·20.5 | — | — | ·42.4 | — | ·45.0 | — | · |
| 5 | $C_8H_{17}$ | $C_6H_{13}$ | " | ·38.2 | — | — | (·30.0) | ·36.3) | — | ·49.7 | · |
| 6 | $C_9H_{19}$ | $C_2H_5$ | " | ·37.0 | — | — | ·37.8 | — | ·52.4 | — | · |
| 7 | $C_9H_{19}$ | $C_4H_9$ | " | ·34.7 | — | — | ·49.1 | ·54.8 | — | — | · |
| 8 | $C_9H_{19}$ | $C_8H_{17}$ | " | ·50.0 | — | — | ·50.8 | ·58.5 | — | ·60.5 | · |
| 9 | $C_{10}H_{21}$ | $CH_3$ | " | ·54.5 | — | — | — | — | (·51.3 | ·51.7) | · |
| 10 | $C_{10}H_{21}$ | $C_5H_{11}$ | " | ·43.1 | ·52.7 | — | — | — | ·55.2 | — | · |
| 11 | $C_{10}H_{21}$ | $C_7H_{15}$ | " | ·49.5 | — | — | ·55.4 | ·58.4 | — | — | · |
| 12 | $C_{10}H_{21}$ | $C_9H_{19}$ | " | ·44.6 | — | — | ·58.9 | ·63.5 | — | — | · |
| 13 | $C_7H_{15}$ | $C_3H_7$ | F | ·31.7 | — | — | — | — | (·17.1) | — | · |
| 14 | $C_8H_{17}$ | $C_6H_{13}$ | F | ·23.4 | — | — | — | — | — | (·21.0) | · |
| 15 | $C_8H_{17}$ | $C_9H_{19}$ | F | ·33.5 | — | — | — | — | — | (·26.7) | · |
| 16 | $C_9H_{19}$ | $C_9H_{19}$ | F | ·33.0 | — | — | — | (·23.9) | — | ·34.7 | · |
| 17 | $C_{10}H_{21}$ | $C_8H_{17}$ | F | ·21.2 | — | — | — | ·29.1 | ·32.1 | ·33.7 | · |

Most of the compounds of the formula (I) are liquid crystalline substances exhibiting smectic phases, and when these compounds are blended with other optically active compounds, preferably liquid crystal compounds, it is possible to obtain a liquid crystal material exhibiting chiral smectic phase within a broad temperature range. Among the compounds of the formula (I), those wherein $R^1$ represents 6 to 12 carbon atoms and $R^2$ represents 1 to 12 carbon atoms are preferred and further among these compounds, those exhibiting smectic C phase are particularly preferred.

The compounds of the formula (I) have a superior compatibility with other optically active liquid crystal compounds i.e. compounds exhibiting SC* phase, SF* phase, SI* phase, SG* phase or SH* phase, compounds exhibiting cholesteric phase, etc.; hence when the compounds of the formula (I) are blended with the latter compounds, they have a superior effectivness of broadening a temperature range wherein SC* phase of chiral smectic liquid crystal compositions is exhibited, particularly a low temperature region thereof.

In the compounds of the formula (I), those wherein X=F are difficult to exhibit smectic phases in the order higher than that of SC phase as compared with those wherein X=H. This means that these compounds alone or in admixture thereof makes it easy to exhibit a broad range of SC phase. Using these compounds, compositions exhibiting SC* phase are easily obtained.

Next, preparation of the compounds of the formula (I) of the present invention will be described.

The compounds of the formula (I) may be prepared through the following passageways:

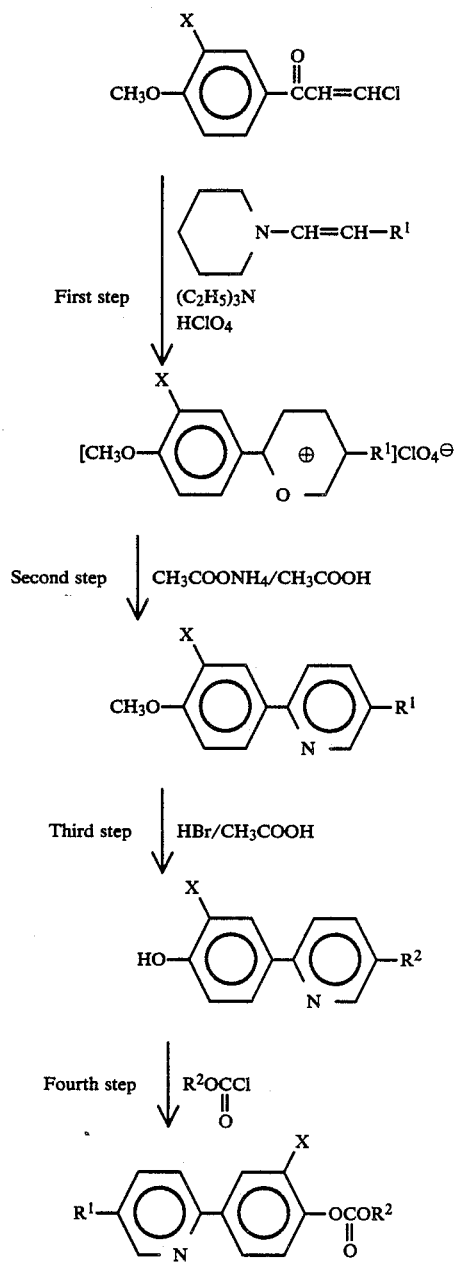

Namely, p-methoxyphenyl β-chlorovinyl ketone (II) as a known substance is reacted with an enamine in the presence of triethylamine in a solvent, followed by further reacting the reaction mixture with perchloric acid to obtain a pyrylium salt (III), reacting this compound (III) with ammonium acetate in a solvent to obtain a compound (IV), further reacting this compound with hydrobromic acid in a solvent to obtain a compound (V), and reacting this compound (V) with an alkyl chloroformate in the presence of pyridine to obtain the objective compound of the formula (I).

The compound and liquid crystal composition of the present invention will be described below in more detail by way of Examples.

EXAMPLE 1

Preparation of 2-(p-nonyloxycarbonyloxy)-5-decylpyridine (a compound of the formula (I) wherein $R^1=C_{10}H_{21}$, $R^2=C_9H_{19}$ and X=H; sample No. 12)

(The first step)

N-dodecenylpiperidine (63.9 g, 0.254 mol) and triethylamine (25.7 g, 0.254 mol) were dissolved in ethyl ether (250 ml) with stirring, followed by dropwise adding to the solution, a solution of β-chlorovinylketone (II) (50 g, 0.254 mol) dissolved in ethyl ether (130 ml) while maintaining the temperature of the system at 35° C. or lower, agitating the mixture at room temperature for 8 hours, adding thereto water (150 ml) and toluene (100 ml), transferring the mixture into a separating funnel, twice washing the resulting organic layer with water, distilling off the solvent under reduced pressure, adding 70% perchloric acid (100 ml) to the residue, adding water (100 ml), heating the mixture under reflux for 10 minutes, cooling the resulting material, washing the resulting crystals with ethyl ether and drying them to obtain 2-(p-methoxyphenyl)-5-decylpyrylium perchlorate (a compound of the formula (III) wherein $R^1=C_{10}H_{21}$ and X=H) (62.8 g). N-dodecenylpiperidine as the raw material was prepared from n-dodecylaldehyde and piperidine according to Mannich et al's method (Chem. Ber. 69, 2106 (1936)).

(The second step)

2-(p-Methoxyphenyl)-5-decylpyrylium perchlorate (62.8 g, 0.147 mol) obtained in the first step, ammonium acetate (113 g, 1.470 mol) and acetic acid (700 ml) were heated under reflux with stirring for 4 hours, followed by pouring the reaction fluid in water, dissolving the formed crystals in toluene, transferring the solution into a separating funnel, three times washing it with water, distilling off the solvent under reduced pressure and recrystallizing the residue to obtain 2-(p-methoxyphenyl)-5-decylpyridine (a compound of the formula (IV) wherein $R^1=C_{10}H_{21}$) (37.2 g) having a m.p. of 61.1°-62.9° C. In addition, compounds of the formula (IV) wherein $R^1$ represents $C_7H_{15}$, $C_8H_{17}$ or $C_9H_{19}$ and X represents H had the following melting points, respectively:

2-(p-methoxyphenyl)-5-heptylpyridine m.p. 54.4°-56.5° C.

2-(p-methoxyphenyl)-5-octylpyridine m.p. 60.7°-62.2° C.

2-(p-methoxyphenyl)-5-nonylpyridine m.p. 55.0°-57.4° C.

(The third step)

2-(p-Methoxyphenyl)-5-decylpyridine (37.2 g, 0.114 mol) obtained in the second step, hydrobromic acid (47%) (80 ml) and acetic acid (500 ml) were heated under reflux for 30 hours, followed by cooling the reaction mixture, pouring it in water, filtering off the resulting crystals, dissolving them in 2N-NaOH aqueous solution (about 150 ml), further adding acetic acid (40 ml) to the resulting solution to acidify it, filtering off the resulting crystals and recrystallizing them from ethanol to obtain 2-(p-hydroxyphenyl)-5-decylpyridine (a compound of the formula (V) wherein $R^1=C_{10}H_{21}$) (27.9 g) having a m.p. of 90.1°–91.7° C. In addition, compounds of the formula (V) wherein $R^1=C_6H_{13}$, $C_7H_{15}$, $C_8H_{17}$ or $C_9H_{19}$ and X=H had the following melting points, respectively:

2-(p-hydroxyphenyl)-5-hexylpyridine m.p. 117.6°–118.0° C.

2-(p-hydroxyphenyl)-5-heptylpyridine m.p. 105.2°–105.9° C.

2-(p-hydroxyphenyl)-5-octylpyridine m.p. 93.2°–95.0° C.

2-(p-hydroxyphenyl)-5-nonylpyridine m.p. 84.6°–87.3° C.

(The fourth step)

2-(p-Hydroxyphenyl)-5-decylpyridine (2 g, 0.006 mol) obtained in the third step, pyridine (50 ml) and nonyl chloroformate (1.5 g, 0.007 mol) were heated under reflux with stirring for 4 hours, followed by cooling the reaction mixture, adding water and toluene, transferring the mixture into a separating funnel, washing the resulting organic layer with 2N-NaOH aqueous solution, further washing it with water, distilling off the solvent under reduced pressure, recrystallizing the residue from ethyl alcohol, filtering off the resulting crystals in a refrigerator and drying them to obtain the objective 2-(nonyloxycarbonyloxyphenyl)-5-decylpyridine (1.5 g). This product had the following phase transition points:

$$C \xrightarrow{44.6° C.} SB \xrightarrow{58.9° C.} SC \xrightarrow{63.5° C.} I$$

Further, its values of elementary analysis accorded well with its calculated values as follows:

| | Observed values (%) | Calculated values (%) (in terms of $C_{31}H_{37}NO_3$) |
|---|---|---|
| C | 78.8 | 78.94 |
| H | 7.7 | 7.91 |
| N | 2.9 | 2.97 |

The above Example was repeated except that 2-(p-hydroxyphenyl)-5-decylpyridine was replaced by other 2-(p-hydroxyphenyl)-5-alkylpyridines and nonyl chloroformate was replaced by other alkyl chloroformates, to obtain other compounds of the formula (I). Their values of physical properties are shown in Table 1 together with those of Example 1.

EXAMPLE 2

Preparation of 2-(m-fluoro-p-nonyloxycarbonyloxyphenyl)-5-nonyl-pyridine (a compound of the formula (I) wherein $R^1=C_9H_{19}$, $R^2=C_9H_{19}$ and X=F)

(i) Sodium methoxide (37.2 g, 0.688 mol) and toluene (2,100 ml) were agitated at room temperature, followed by dropwise adding to the mixture, a solution of m-fluoro-p-methoxyacetophenone (150.1 g, 0.625 mol) as a known substance, ethyl formate (46.3 g, 0.625 mol) and toluene (700 ml), keeping the resulting mixture at room temperature for 8 hours, adding water (500 ml), transferring the resulting mixture into a separating funnel, adding to the aqueous solution, a solution of conc. sulfuric acid (25 ml) and water (500 ml) dissolving deposited crystals in fresh toluene, drying the toluene solution with calcium chloride, further slowly dropwise adding thionyl chloride (150 ml) under cooling, heating the mixture under reflux for one hour, distilling off the solvent and excess thionyl chloride under reduced pressure and recrystallizing the residue from heptane to obtain m-fluoro-p-methoxyphenyl β-chlorovinyl ketone (a compound of the formula (II) wherein X=F) (83 g).

(ii) Using undecenylpiperidine (76 g, 0.32 mol), triethylamine (32.4 g, 0.32 mol) and m-fluoro-p-methoxyphenyl β-chlorovinyl ketone (63.3 g, 0.32 mol) obtained in the above step (i), operation was carried out in the same manner as in Example 1 to obtain 2-(m-fluoro-p-methoxyphenyl)-5-nonyl-pyrylium perchlorate (a compound of the formula (III) wherein X=F and $R^1=C_9H_{19}$) (55 g).

(iii) Using 2-(m-fluoro-p-methoxyphenyl)-5-nonyl-pyrylium perchlorate (55 g, 0.139 mol) obtained in the above step (ii), ammonium acetate (107 g, 1.39 mol) and acetic acid (500 ml), operation was carried out in the same manner as in Example 1 to obtain 2-(m-fluoro-p-methoxyphenyl)-5-nonyl- pyridine ( a compound of the formula (IV) wherein X=F and $R^1=C_9H_{19}$) (25 g) having a m.p. of 47.5°–48.7° C.

In addition, compounds of the above formula (IV) wherein X=F and $R_1=C_6H_{13}$, $C_7H_{15}$, $C_8H_{17}$ or $C_{10}H_{21}$ had the following melting points, respectively: 52.6°–53.7° C.; 49.1°–51.2° C.; 46.3°–48.3° C. or 53.5°–55.6° C.

(iv) Using 2-(m-fluoro-p-methoxyphenyl)-5-nonyl-pyridine (23 g, 0.07 mol) obtained in the step (iii), hydrobromic acid (47%, 123 ml) and acetic acid (285 ml), operation was carried out in the same manner as in Example 1 to obtain 2-(m-fluoro-p-hydroxyphenyl)-5-nonyl-pyridine (a compound of the formula (V) wherein X=F and $R^1=C_9H_{19}$) (16.7 g) having a m.p. of 45.5°–47.0° C.

In addition, compounds of the formula (V) wherein X=F and $R^1=C_6H_{13}$, $C_7H_{15}$, $C_8H_{17}$ or $C_{10}H_{21}$ had the following melting points, respectively: 100.7°–103.0° C.; 83.7°–86.1° C.; 73.5°–74.6° C. or 46.8°–48.3° C.

(v) 2-(m-Fluoro-p-hydroxyphenyl)-5-nonylpyridine obtained in the step (iv) (2.0 g) was dissolved in pyridine (100 ml), followed by dropwise adding to the solution, nonyl chloroformate (2.0 g), allowing the mixture to stand at room temperature overnight, extracting the resulting material with toluene, washing the resulting organic layer with 2N-NaOH aqueous solution, further washing it with water till the washing water became neutral, distilling off the solvent and recrystallizing the residue from ethanol to obtain the objective 2-(m-fluoro-p-nonyloxycarbonyloxyphenyl)-5-nonylpyridine (1.0 g).

The phase transition points of this product were as follows:

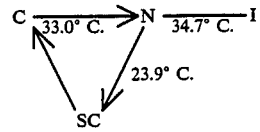

Using other 2-(m-fluro-p-hydroxyphenyl)-5-alkyl-pyridines in place of 2-(m-fluor-p-hydroxyphenyl)-5-nonyl pyridine, and also using various alkyl chloroformates in place of nonyl chloroformate, operations were carried out in the same manner as above, compounds of the formula (I) wherein X=F were obtained. Representative values of the physical properties of these compounds are shown in Table 1.

EXAMPLE 3
(Composition)

Using the liquid crystal compounds of the present invention listed in Table 1, the following mixture was prepared:

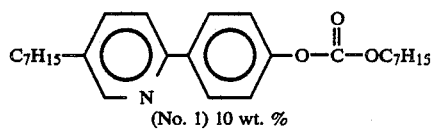
(No. 1) 10 wt. %

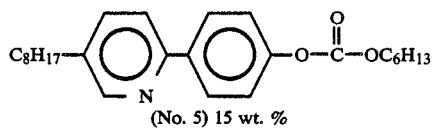
(No. 5) 15 wt. %

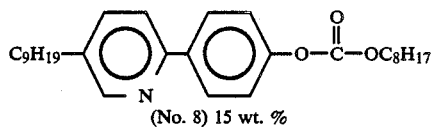
(No. 8) 15 wt. %

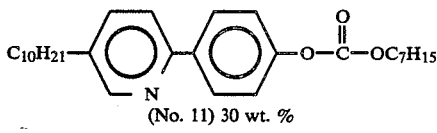
(No. 11) 30 wt. %

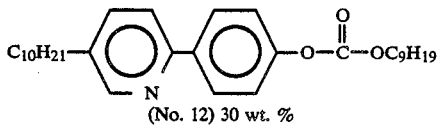
(No. 12) 30 wt. %

The above mixture has a m.p. of 25.0° C., and forms SB phase on the higher temperature side, SC phase at 46.0° C., N phase at 53.2° C. and an isotropic liquid at 56.8° C.

To 60% by weight of the above mixture were added the following two kinds of chiral smectic liquid crystal compounds to prepare a chiral smectic liquid crystal composition:

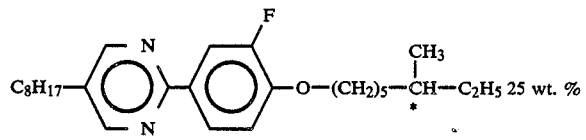

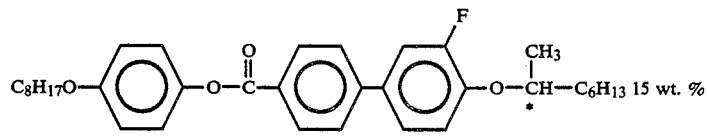

The resulting chiral smectic omposition was filled in a cell of 2 μm thick provided with transparent electrodes each obtained by applying PVA (polyvinyl alcohol) as an aligning agent onto the surface and further subjecting the resulting surface to a parallel aligning treatment by rubbing the surface and the resulting liquid crystal cell was provided between a polarizer and an analyzer crossed to one another. When a voltage of 15 V was impressed to the element, change in the intensity of transmitted light was confirmed.

The response time was sought from the change in the intensity of transmitted light at that time to give about 300 μsec at 25° C.

The above-mentioned liquid crystal composition had a m.p. of 3.0° C., exhibited SC* phase at a region of higher temperatures than the m.p. and formed SA phase at 51.6° C., N phase at 52.0° C. and an isotropic liquid at 56.5° C. Further, its supercooled state was observed down to −32.0° C. and it had SC* phase down to this temperature and also no other smectic phase was observed.

In addition, it had a spontaneous polarization value at 25° C. of 6 nC/cm$^2$ and a tilt angle of 26.6° C.

As seen from the foregoing, when the compounds expressed by the formula (I) are blended with optically active compounds, ferroelectric chiral smectic liquid crystal compositions having properties suitable to practical uses are obtained.

EXAMPLE 4

A composition consisting of the following compounds of the present invention was prepared:

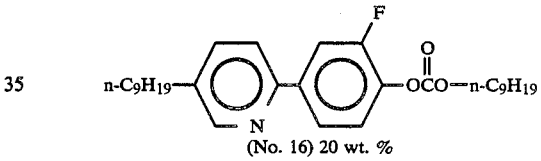
(No. 16) 20 wt. %

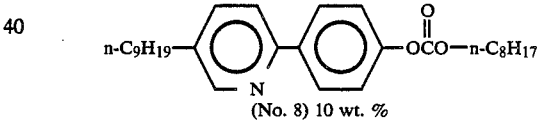
(No. 8) 10 wt. %

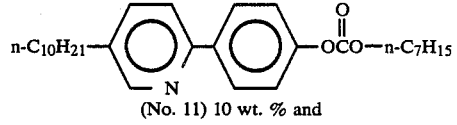
(No. 11) 10 wt. % and

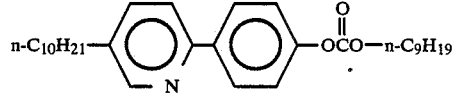

(No. 12) 60 wt. %

This composition had a m.p. of 24.6° C. and formed SB phase on the higher temperature side thereof, SC phase at 44.5° C. and an isotropic liquid at 57.2° C.

To 60% by weight of the above composition were added the following two optically active compounds to constitute a chiral smectic liquid crystal composition:

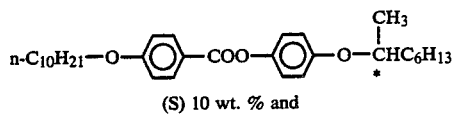

(S) 10 wt. % and

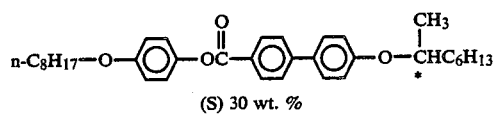

(S) 30 wt. %

While the m.p. of this composition was unclear, it exhibited SC* phase up to 57.5° C., and formed cholesteric phase on the higher temperature side thereof and an isotropic liquid at 67.0° C. With this composition, the response time was sought in the same manner as in Example 3 to give about 290 μsec at 25° C. The value of the spontaneous polarization was 10 nC/cm$^2$ at 25° C. and the the tilt angle was 28.5° C.

What we claim is:

1. A liquid crystal compound expressed by the formula

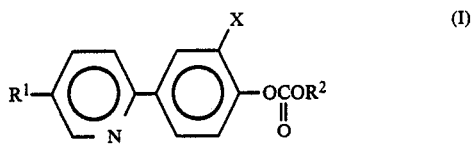

wherein $R^1$ and $R^2$ each represent an alkyl group of 1 to 20 carbon atoms and X represents hydrogen atom or fluorine atom.

2. A liquid crystal compound according to claim 1 wherein $R^1$ represents an alkyl group of 6–12 carbon atoms and $R^2$ represents an alkyl group of 1–12 carbon atoms in said formula (I).

3. A chiral smectic liquid crystal composition comprising at least one kind of the liquid crystal compounds of said formula (I) of claim 1 and an optically active compound.

4. A chiral smectic liquid crystal composition according to claim 3 wherein the chiral smectic phase of the composition is chiral smectic C phase.

5. A chiral smectic liquid crystal composition according to claim 3 wherein said optically active compound is an optically active liquid crystal compound.

6. A chiral smectic liquid crystal composition according to claim 5 wherein said optically active compound is a chiral smectic liquid crystal compound.

7. A ferroelectric light switching element containing a chiral smectic liquid crystal composition of claim 3.

* * * * *